United States Patent [19]
Nordmann et al.

[11] Patent Number: 5,218,074
[45] Date of Patent: Jun. 8, 1993

[54] CROSS-LINKED EPOXY RESINS WITH NON-LINEAR OPTICAL PROPERTIES

[75] Inventors: Jens Nordmann, Neunkirchen; Heinz Hacker, Nuernberg, both of Fed. Rep. of Germany

[73] Assignees: Siemens Aktiengesellschaft, Berlin; Siemens Aktiengesellschaft, Munich, both of Fed. Rep. of Germany

[21] Appl. No.: 760,957

[22] Filed: Sep. 17, 1991

[30] Foreign Application Priority Data

Sep. 24, 1990 [DE] Fed. Rep. of Germany ....... 4030179

[51] Int. Cl.$^5$ ................ C08G 59/00; C08G 65/08; C08G 65/14
[52] U.S. Cl. .................... 528/96; 528/98; 528/99; 528/100; 528/101; 528/361; 549/549; 549/551; 549/557; 549/556; 549/560
[58] Field of Search ............. 528/96, 98, 361, 99, 528/100, 101; 549/549, 551, 557, 556, 560

[56] References Cited

U.S. PATENT DOCUMENTS

| | | | |
|---|---|---|---|
| 3,373,140 | 3/1968 | Aftergut | 525/523 |
| 3,383,360 | 5/1968 | Harrison | 528/106 |
| 5,112,934 | 5/1992 | Kester et al. | 525/481 |

FOREIGN PATENT DOCUMENTS

0231770 8/1987 European Pat. Off. .
0262680 4/1988 European Pat. Off. .

OTHER PUBLICATIONS

"Makromol. Chem.", Bd. 190 (1989), pp. 2673–2681.
"Macromolecules", vol. 21 (1988), pp. 2899–2901.
"J. Appl. Phys.", vol. 66 (1989), pp. 3241–3247.
"Appl. Phys. Lett.", vol. 56 (1990), pp. 2610–2612.
"J. Opt. Soc. Am. B", vol. 7 (1990), pp. 1239–1250.
"J. Opt. Soc. Am. B", vol. 6, (1989), pp. 685–692.
"macromolecules", vol. 15 (1982), pp. 1385–1389.
"Appl. Phys. Lett.", vol. 49 (1986), pp. 248–250.
"Electron. Lett." vol. 23 (1987), pp. 700–701.

*Primary Examiner*—John C. Bleutge
*Assistant Examiner*—Frederick Krass
*Attorney, Agent, or Firm*—Kenyon & Kenyon

[57] ABSTRACT

The invention provides epoxy resins having the following structure:

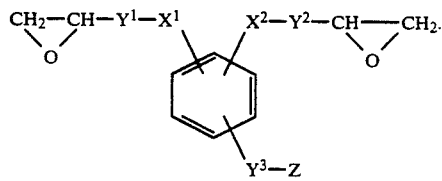

The cross-linked epoxy resins have non-linear optical properties.

The group "Z" constitutes a nonlinear optical chromophone having stilbene, azo, azomethine or propargyl moieties as linking units.

5 Claims, No Drawings

CROSS-LINKED EPOXY RESINS WITH NON-LINEAR OPTICAL PROPERTIES

BACKGROUND OF THE INVENTION

1. Field of the Invention

The invention relates to new epoxy resins and their use.

2. Description of Related Art

Non-linear optics deals with the interaction of the electromagnetic field of a light wave spreading in a medium with this medium, as well as with the related occurrence of new fields with changed properties. Specifically, if the electromagnetic field enters into interaction with the medium, which consists of one molecule or of many molecules, then this field polarizes the molecules.

Polarization, which is induced by a local electrical field in a molecule, can be represented as the power series of the electrical field intensity - corresponding to Equation (1):

$$P = \alpha.E + \beta.E^2 + \gamma.E^3 + \cdots \quad (1)$$

P is the induced polarization and E is the induced local electrical field, and $\alpha$, $\beta$ and $\gamma$-represent the polarizability of the first, second and third order.

On a macroscopic level, a similar relation holds true—according to Equation (2)—for polarization induced, by an external electrical field, in a medium consisting of several molecules:

$$P = \epsilon_0(\chi^{(1)}.E + \chi^{(2)}.E^2 + \chi^{(3)}.E^3 + \ldots) \quad (2);$$

again, P is the induced polarization and E is the induced local electrical field, $\epsilon_0$ is the dielectric constant, and $\chi^{(1)}$, $\chi^{(2)}$ and $\chi^{(3)}$ represent the dielectric susceptibility of the first, second and third order.

The dielectric susceptibilities in Equation (2) have a meaning similar to that of the molecular coefficients in Equation (1): They are material constants, which are dependent on the molecular structure and the frequency, and, in general also on the temperature. The coefficients $\chi^{(2)}$ and $\chi^{(3)}$ cause a great number of non-linear optical effects, specifically depending on the input frequency and the distance of the molecular oscillation frequencies or electronic resonances, and the input frequencies or frequency combinations, as well as the phase adaptation conditions.

Materials with a dielectric susceptibility of the second order are suited for frequency doubling (SHG=Second Harmonic Generation); this is the transformation of light with a frequency $\omega$ into light with a frequency $2\omega$. Another non-linear optical effect of the second order is the linear electro-optical effect (Pockels Effect); it results from the change in the index of refraction of the optical medium when an electrical field is applied. Optical rectification as well as sum and difference frequency mixing are further examples of non-linear optical effects of the second order.

Areas of use for materials of the type stated above are, for example, electro-optical switches as well as areas of data processing and integrated optics, such as optical chip-to-chip connections, wave-guiding in electro-optical layers, Mach Zehnder interferometers and optical signal processing in sensor technology.

Materials with a dielectric susceptibility of the third order are suited for frequency tripling of the incident light wave. Additional effects of the third order are optical bistability and phase conjugation. Concrete application examples are purely optical switches for constructing purely optical computers and holographic data processing.

To achieve a sufficient non-linear optical effect of the second order, the dielectric susceptibility of the second order $\chi^{(2)}$ must be greater than $10^{-9}$ electrostatic units (esu); this means that the hyperpolarizability B must be greater than $10^{-30}$ esu. Another fundamental prerequisite for achieving a non-linear optical effect of the second order is the non-centrosymmetrical orientation of the molecules in the non-linear optical medium; otherwise, $\chi^{(2)} = 0$. This can be achieved with an orientation of the molecular dipoles, if it is not predetermined by the crystal structure, as in the case of crystalline materials. Thus, the greatest values for $\chi^{(2)}$ for a non-linear optical medium have been achieved by orientation of the molecular dipoles in electrical fields.

Inorganic materials, such as lithium niobate ($LiNbO_3$) and potassium dihydrogen phosphate ($KH_2PO_4$), demonstrate non-linear optical properties. Semiconductor materials such as gallium arsenide (GaAs), gallium phosphide (GaP) and indium antimonide (InSb), also demonstrate non-linear optical properties.

However, along with the advantage of a high electro-optical coefficient of the second order, inorganic materials of the type stated have some major disadvantages. For example, the processing of these materials is very complicated in terms of technology, since individual process steps are time-consuming and must be carried out with extremely high accuracy (see in this regard: C. Flytzanis and J. L.. Oudar "Nonlinear Optics: Materials and Devices," Springer-Verlag (1986), pages 2 to 30). These materials are furthermore unsuitable for those electro-optical components which work at high modulation frequencies. Due to the high dielectric constants which are intrinsically present, the dielectric losses which occur at high frequencies (above several GHz) are so high that working at these frequencies is impossible (see in this regard: "J. Opt. Soc. Am. B," Vol. 6 (1989), pages 685 to 692).

It is known that organic and polymer materials with extended $\pi$ electron systems, which are substituted with electron donors and acceptors, demonstrate non-linear optical properties, i.e. can be used in non-linear optical media (see in this regard: R. A. Hann and D. Bloor "Organic Materials for Non-linear Optics," The Royal Society of Chemistry (1989), pages 382 to 389 and 404 to 411).

Monocrystals on an organic basis demonstrate a high electro-optical coefficient of the second order and good photochemical stability, in comparison with $LiNbO_3$; the required high level of orientation of the non-linear optical molecules is also already present. Some significant criteria, however, speak against technical utilization of this material class. For example, production of the monocrystals, specifically both from solution and from a melt, requires a time of 14 to 30 days (see in this regard: D. S. Chemla and J. Zyss "Nonlinear Optical Properties of Organic Molecules and Crystals," Academic Press, Inc. (1987), Vol. 1, pages 297 to 356); the production process therefore does not meet the requirements of technical production. Furthermore, the melting point of the crystals lies at 100° C., on the average, so that it would not be possible to achieve a working temperature range up to 90° C. Furthermore, organic crystals cannot be structured and their lateral dimensions are presently still too small to allow them to be constructed as an electro-optical component.

For applications of non-linear optics in the areas of data transmission and integrated optics, polymer materials have found increasing importance recently. For this purpose, an external electrical field is applied to polymer materials heated above the glass transition temperature; this results in orientation of the non-linear optical molecules. After cooling (below the glass transition temperature), with the electrical field applied, anisotropic and therefore non-centrosymmetrical polymers are obtained, which demonstrate dielectric susceptibilities of the second order.

Non-linear optical compounds which are dissolved or diffused in polymers can be processed to form thin layers, in this manner, as is required by integrated optics (see in this regard: "Macromolecules," Vol. 15 (1982), pages 1385 to 1389; "Appl. Phys. Lett.," Vol 49 (1986), pages 248 to 250; "Electron. Lett.," Vol. 23 (1987), pages 700 and 701). However, the low solubility of the compounds with a low molecular weight, their insufficient distribution in the polymers, the migration of the active molecules out of the polymer matrix and the loss of the non-centrosymmetrical orientation of the active molecule species over a period of only a few hours, even at room temperature, are disadvantageous in this connection.

Polymers with covalently bonded non-linear optical molecule components, which simultaneously have a liquid-crystalline character, are also known as non-linear optical compounds (see in this regard: EP-OS 0 231 770 and EP-OS 0 262 680). While these materials do not demonstrate the disadvantages stated above, they are not suited for applications in electro-optics and integrated optics in their current stage of development, since optical losses>20 dB/cm, caused by the inherent domain scattering, occur here. Furthermore, studies of amorphous non-linear optical polymers have already been reported (see: "Macromolecules," Vol. 21 (1988), pages 2899 to 2901).

Both with liquid-crystalline polymers and with amorphous polymers with covalently bonded non-linear optical molecule units, a high concentration of such units can be achieved. A spacer thereby uncouples the molecular mobility of the non-linear optical units from the polymer chain; at the same time however, the glass transition temperature decreases drastically. However, with this, a loss of the molecular orientation of the non-linear optical molecule units and a loss of the non-linear optical activity must be expected at use temperatures in the range of the glass transition temperature of the polymers.

SUMMARY OF THE INVENTION

It is an object of the invention to expand the available supply of polymers for non-linear optical media and, in particular, to make polymers available which demonstrate a technically sufficient glass transition temperature.

This is accomplished, according to the invention, with epoxy resins with the following structure:

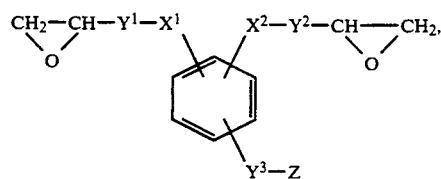

where the following applies:

$X^1$ and $X^2$=O, S, COO or OOC;

$Y^1$ and $Y^2$=alkylene (linear or branched) with 1 to 3 C atoms;

$Y^3$=alkylene (linear or branched) with 2 to 20 C atoms, where one or more non-adjacent $CH_2$ groups, with the exception of the binding $CH_2$ group to the group Z, can be replaced with O, S or NR (R= H or $C_1$ to $C_6$ alkyl);

Z is a conjugated x electron system (E) with the structure —D—E—A, substituted with an electron donor (D) and an electron acceptor (A), where the following applies:

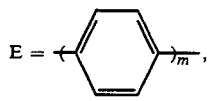

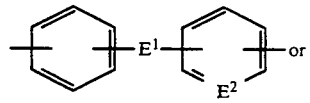

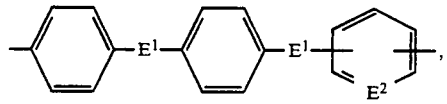

with
m=1 to 3,
$E^1$=—$(CH=CH)_n$—, —N=N—, —CH=N—, —N=CH— or —C≡C—, with n=1 to 3, and
$E^2$=CH or N;
D=O, S, $NR^1$, $PR^2$ or $NR^3$—$NR^4$,
with $R^1$, $R^2$, $R^3$ and $R^4$=hydrogen, alkyl, alkenyl, aryl or heteroaryl; and
A=halogen, NO, $NO_2$, CN, $CF_3$, $COR^5$, $COOR^6$, $SO_2OR^7$, $SO_2NR_2^8$,

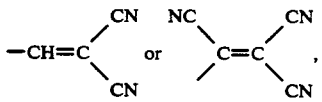

with $R^5$, $R^6$, $R^7$ and $R^8$=hydrogen, alkyl, alkenyl, aryl or heteroaryl.

Preferably, the following applies:
$X^1$=$X^2$=O or COO,
$Y^1$=$Y^2$=$CH_2$
$Y^3$=O—$(CH_2)_o$, with o=2 to 6, and
Z=—D—E—A with D=O or $NR^1$, A=$NO_2$ or

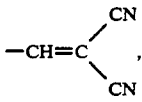

and

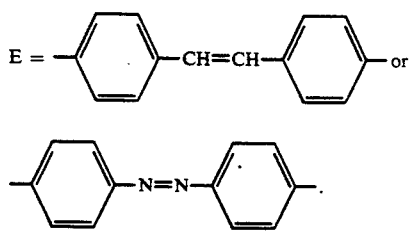

The conjugated π electron systems (E) can be substituted with at least one more electron donor on the electron donor side, in addition to D, and at least one more electron acceptor on the electron acceptor side in addition to A. These substituents should be selected in such a way that the total of the Hammet constants o of the additional substituents in each case does not exceed the value of the existing substituents (D or A). The invention therefore provides new epoxy resins of the type stated above. Furthermore, the invention provides for the use of these epoxy resins in cross-linked form, for non-linear optical media, i.e. for non-linear optical polymers in the form of cross-linked epoxy resins with the preceding structure.

It was surprisingly found that cross-linked epoxy resins of the type described, with covalently bonded non-linear optical molecule units, on the one hand do not demonstrate the disadvantages stated above, but on the other hand do possess the known good polymer-specific properties, such as the ability to be processed to form thin layers, in the μm range, high concentration of non-linear optical molecule units, low optical attenuation and technically sufficient glass transition temperature. This is due to the fact that in the epoxy resins according to the invention, structuring of the non-linear optical polymer layer to form wave-guide structures can take place by cross-linking, something that is not possible with non-cross-linked polymers.

The production of non-linear optical polymers by cross-linking according to chemical methods is already known (see in this regard: "J. Appl. Phys.," Vol. 66 (1989), pages 3241 to 3247). For this purpose, soluble prepolymers are first formed by reaction of bisphenol A diglycidyl ether with 4-nitro-1,2-phenylene diamine, which are then converted to insoluble cross-linked polymers by being heated. In a corresponding manner, non-linear optical polymers can also be produced from N,N-diglycidyl-4-nitroaniline and N-(2-aminophenyl)-4-nitroaniline (see in this regard: "Appl. Phys. Lett.," Vol. 56 (1990), pages 2610 to 2612). Furthermore, electro-optical polymer films which are obtained from reaction of 4-nitroaniline with bisphenol A diglycidyl ether are known from "J. Opt. Soc. Am. B," Vol 7 (1990). pages 1239 to 1250.

The production of epoxy resins according to the invention as well as the synthesis of the prestages takes place according to known methods (cf. in this regard the examples). Cross-linking of the epoxy resins according to the invention can take place either thermally or photochemically.

For thermal cross-linking, reagents which cause cross-linking are added to the epoxy resins according to the invention, in a corresponding molar ratio; in general, these are compounds with acidic hydrogen atoms, substances from which such compounds can be produced, or compounds with electrophilic groupings. Cross-linking then takes place at a raised temperature, preferably at a temperature which lies 15° C. above the glass transition temperature of the cross-linked end product, i.e. of the polymer. If necessary, the cross-linking reaction can be catalyzed with the addition of an accelerator. The compounds or substances used for thermal cross-linking are known. Preferably, carboxylic acid anhydrides, phenols and aliphatic, cycloaliphatic or aromatic amines are used for this.

Suitable carboxylic acid anhydrides are, in particular, phthalic acid anhydride, tetrahydrophthalic, hexahydrophthalic, methyltetrahydrophthalic and endomethylene tetrahydrophthalic acid anhydride, pyromellithic acid, trimellithic acid and benzophenone tetracarboxylic acid anhydride, as well as maleic acid anhydride/styrene copolymers. Amines that can be used are, in particular, 4,4'-diaminodiphenyl methane, as well as its o,o'-alkyl substituted derivatives and hydrogenated 4,4'-diaminodiphenyl methane, 4,4'-diaminodiphenyl ether, 4,4'-diaminodiphenyl sulfone, 2,4-diamino-3,5-diethyl toluene, isophoron diamine, diethylene triamine, triethylene tetramine and polyaminoamides on the basis of diethylene triamine.

Photochemical cross-linking of the epoxy resins according to the invention takes place using light with a shorter wave length, preferably light in the UV spectrum (290 to 390 nm) To trigger photochemical cross-linking, initiators are added, which release Lewis or Bronsted acids under the influence of light; such compounds are known. Preferably, aryl diazonium, diaryl iodonium or triaryl sulfonium salts, which have tetrafluoroborate, hexafluorophosphate or hexafluoroantimonate as the anion, as well as arene iron salts, are used as initiators.

To improve the surface quality, the processability and/or the compatibility with polymers, processing aids can be added to the epoxy resins, depending on their purpose of use. These are, for example, thixotropic agents, flow agents, plasticizers, cross-linking agents, lubricants and binders.

The epoxy resins according to the invention are applied to a substrate in dissolved or liquid form, if necessary together with compounds that cause cross-linking, or initiators, by centrifugation, dipping, printing or spreading. In this manner, a non-linear optical arrangement is obtained, where the epoxy resins or corresponding prepolymers are oriented in dipolar manner in electrical fields, before and/or after cross-linking. After cooling, polymer materials with excellent non-linear optical properties are obtained, and, due to the cross-linking, they have increased orientation stability and thus greater long-term stability, even at higher use temperatures.

To produce the non-linear optical media, it is particularly advantageous to use oligomer prepolymers, with a low molecular weight, of the epoxy resins according to the invention. The production of these prepolymers takes place in known manner, where the epoxy resins are brought to reaction with a shortage of the compound which causes cross-linking. After application to a substrate, the prepolymers are oriented in dipolar manner - above the glass transition temperature—and subsequently cross-linked to yield the non-linear optical polymers (with an improved property profile).

On the basis of embodiments, the invention will be explained in greater detail below with reference to the following illustrative examples.

EXAMPLE 1

Production of 4-hydroxy-4'-nitrostilbene 72.4 g p-nitrophenyl acetic acid and 48.8 g p-hydroxybenzaldehyde are heated, to 140° C., together with 60 ml piperidine, while stirring. After the reaction is complete, the cooled mass is recrystallized from glacial acetic acid (melting point: 207° C.); yield: 70%.

EXAMPLE 2

Production of 4-(6-bromohexyloxy)-4'-nitrostilbene 120.6 g 4-hydroxy-4'-nitrostilbene (see Example 1), 153.8 ml 1.6-dibromohexane and 96.5 g potassium carbonate are heated in absolute acetone, together with a small amount of potassium iodide, for 48 h, under reflux. After cooling, the inorganic salts are filtered off, the solvent is removed in a vacuum and the residue is recrystallized from ethanol (melting point: 101° C.); yield: 60%.

EXAMPLE 3

Production of 5-[4-(6-oxyhexyloxy)-4'-nitrostilbene]-isophthalic acid dimethyl ester 60.6 g 4-(6-bromohexyloxy)-4'-nitrostilbene (see Example 2), 37.8 g 5-hydroxyisophthalic acid dimethyl ester and 29 g potassium carbonate are heated in absolute acetone, together with a small amount of potassium iodide, for 72 h, under reflux. The precipitated solid is filtered off hot, dissolved in methylene chloride and chromatographed on silica gel (melting point: 135° C.); yield: 80%.

EXAMPLE 4

Production of 5-[4-(6-oxyhexyloxy)-4'-nitrostilbene]-isophthalic acid 10 g 5-[4-(6-oxyhexyloxy)-4'-nitrostilbene]-isophthalic acid dimethyl ester (see Example 3) and 150 ml 10% caustic soda solution are heated together for 3 h, under reflux. After cooling, the reaction solution is adjusted to a pH-value of 1 to 2 with concentrated hydrochloric acid, the precipitate is filtered off, washed neutral with water, dried and recrystallized from ethanol (melting point: 210° C.); yield: 96%.

EXAMPLE 5

Production of 5-[4-(6-oxyhexyloxy)-4'-nitrostilbene]-isophthalic acid diglycidyl ester 10.9 g 5-[4-(6-oxyhexyloxy)-4'-nitrostilbene]-isophthalic acid (see Example 4) is suspended in 40 g epichlorhydrine, mixed with 43.2 mg benzyltriethyl ammonium chloride and stirred at 105° C. for 4 h. Subsequently, the mixture is heated under reflux, and then 3 ml 50% caustic soda solution is dripped in such a way that water is continuously removed, azeotropically, from the reaction mixture. After addition of the caustic completed, heating is continued for another 15 min, in order to remove the last residue of water. After cooling, the reaction mixture is mixed with ethyl acetate, the precipitated residue is filtered off and recrystallized from toluene (melting point: 160° C.); yield: 85%.

EXAMPLE 6

For cross-linking of the glycidyl-functionalized non-linear optical molecule units, the isophthalic acid ester according to Example 5—with the addition of 1 mole-% N,N'-dimethylbenzylamine—is mixed with carboxylic acid anhydrides and hardened at a raised temperature. The results obtained are summarized in Table 1 ($T_G$ = glass transition temperature), where the following applies:

EP = 5-[4-(6-oxyhexyloxy)-4'-nitrostilbene]-isophthalic acid diglycidyl ester
BSA = succinic acid anhydride
HHPSA = hexahydrophthalic acid anhydride
PSA = phthalic acid anhydride
PMSA = pyromellithic acid anhydride

TABLE 1

| Polymer No. | Composition in mole-% | Hardening temperature in °C. | $T_G$ in °C. |
| --- | --- | --- | --- |
| 1 | 100 EP:100 BSA | 140 | 110 |
| 2 | 100 EP:100 HHPSA | 140 | 124 |
| 3 | 100 EP:100 PSA | 140 | 127 |
| 4 | 100 EP:50 PMSA | 150 | 137 |

EXAMPLE 7

For the electro-optical studies, the epoxy resins according to the invention or corresponding prepolymers, if necessary together with compounds which cause cross-linking, in a suitable solvent, are applied to ITO-coated glass (ITO = indium-tin-oxide) by spin-coating; the layer thickness of the films produced in this manner is usually 3 to 6 $\mu$m. For electrical poling, to achieve a high level of non-centrosymmetrical orientation, a gold electrode is sputtered onto the film (of the epoxy resin); the counter-electrode is the light-permeable ITO layer. After heating of the sample to the glass transition temperature range, a constant voltage is applied, where the required voltage increase is adjusted to the orientation behavior of the non-linear optical molecule units, in order to avoid electrical punctures and therefore a destruction of the film. After a poling field intensity of 50 to 100 V/$\mu$m has been reached, a poling period of 15 min is sufficient for orientation of the non-linear optical molecule units. Subsequently, the sample is cross-linked, either thermally (corresponding to Example 6) or photochemically, and then the sample is cooled to room temperature, with a constant electrical field applied to it, causing the orientation to become fixed.

Electro-optical examination of the polymer samples takes place by interferometric measurement of a laser beam applied at an angle, after single reflection at the gold electrode. The measurement setup required for this, and the measurement evaluation, are known (see, for example: "Appl. Phys. Lett.," Vol. 56 (1990), pages 1734 to 17361. The electro-optical coefficients $r_{33}$ of the polymers according to Example 6, i.e. of the cross-linked epoxy resins, which relate to a poling field intensity of 70 V/$\mu$m, are summarized in Table 2.

TABLE 2

| Polymer No. | Electro-optical coefficient in pm/V |
| --- | --- |
| 1 | 4.2 |
| 2 | 3.2 |
| 3 | 3.4 |
| 4 | 3.5 |

What is claimed is:

1. An epoxy resin having the structure:

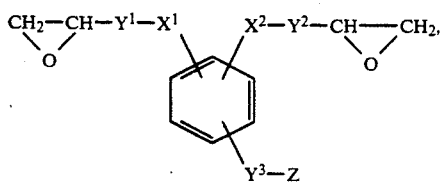

where the following applies:
$X^1$ and $X^2 = O$, S, COO or OOC;
$Y^1$ and $Y^2 =$ alkylene (linear or branched) with 1 to 3 C atoms;
$Y^3 =$ alkylene (linear or branched) with with 2 and 20 C atoms,
Z is a conjugated π electron system with the structure —D—E—A, where the following applies:

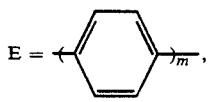

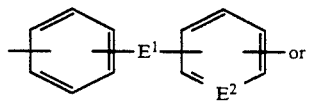

with
m = 1 to 3,
$E^1 = -(CH=CH)_n-$, $-N=N-$, $-CH=N-$, $-N=CH-$ or $-C\equiv C-$, with n = 1 to 3, and
$E^2 = CH$ or N;
$D = O$, S, $NR^1$, $PR^2$ or $NR^3-NR^4$, with $R^1$, $R^2$, $R^3$ and $R^4 =$ hydrogen, alkyl, alkenyl, aryl or heteroaryl; and
A = halogen, NO, $NO_2$, CN, $CF_3$, $COR^5$, $COOR^6$, $SO_2OR^7$, $SO_2NR^8_2$,

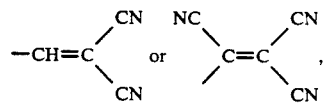

with $R^5$, $R^6$, $R^7$ and $R^8 =$ hydrogen, alkyl, alkenyl, aryl or heteroaryl.

2. The epoxy resin according to claim 1, wherein the following applies:
$X^1 = X^2 = O$ or COO,
$Y^1 = Y^2 = CH_2$
$Y^3 = O-(CH_2)_o$, with o = 2 = to 6, and
Z = —D—E—A with D = O or $NR^1$, A = $NO_2$ or

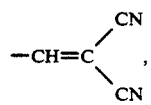

and

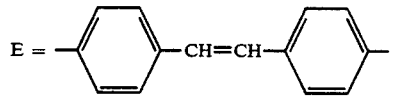

or

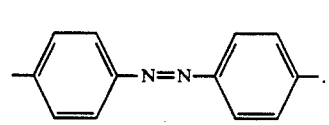

3. The epoxy resin according to claim 1 in cross-linked form.

4. The epoxy resin according to claim 2 in cross-linked form.

5. The epoxy resin according to claim 1 wherein in the alkylene group $Y^3$ one or more non-adjacent $CH_2$ groups, other than the binding $CH_2$ group to the group Z, are replaced with O, S or NR, with R = H or $C_1$ to $C_6$ alkyl.

* * * * *